United States Patent [19]

Blank et al.

[11] Patent Number: 5,095,133

[45] Date of Patent: Mar. 10, 1992

[54] PROCESS FOR THE PREPARATION OF AMINOMETHYLENE COMPOUNDS

[75] Inventors: Heinz U. Blank, Odenthal; Helmut Kraus, Cologne, both of Fed. Rep. of Germany

[73] Assignee: Bayer Aktiengesellschaft, Leverkusen, Fed. Rep. of Germany

[21] Appl. No.: 552,660

[22] Filed: Jul. 16, 1990

[30] Foreign Application Priority Data

Aug. 3, 1989 [DE] Fed. Rep. of Germany ....... 3925720

[51] Int. Cl.$^5$ ................ C07C 253/30; C07C 211/21; C07C 67/00
[52] U.S. Cl. .................... 558/375; 544/161; 544/162; 544/163; 544/171; 546/192; 546/230; 546/238; 548/566; 548/571; 548/572; 558/384; 560/9; 560/22; 560/23; 560/38; 560/41; 560/43; 560/147; 560/156; 560/170; 560/171
[58] Field of Search ...... 558/375; 560/9, 22, 560/23, 38, 41, 43, 147, 171

[56] References Cited

FOREIGN PATENT DOCUMENTS 0151624 6/1980 Fed. Rep. of Germany .
257067 1/1987 Fed. Rep. of Germany .
917436 2/1963 United Kingdom .

OTHER PUBLICATIONS

Chemische Berichte, vol. 96; 1963, H. Brederek et al; Uber Säureamid-Dialkylsulfat-komplexe, pp. 1350–1355.
Chemical Abstracts, vol. 93, Aug. 4, 1980; W. Kantlehner et al., Orghoamides, XXXII, Reaction of tert-butoxy-N,N,N', N-tetramethylmethanediamine with NH- and CH- acidic compounds, pp. 854–855.

*Primary Examiner*—Joseph Paul Brust
*Attorney, Agent, or Firm*—Sprung Horn Kramer & Woods

[57] ABSTRACT

Aminomethylene compounds of the formula

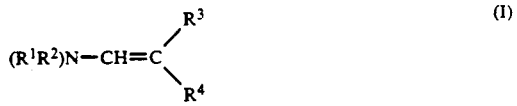

(I)

can be prepared by reaction of C-H acid compounds of the formula

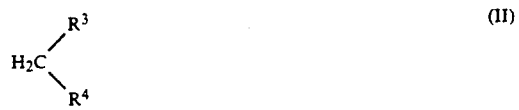

(II)

with salts of the formula

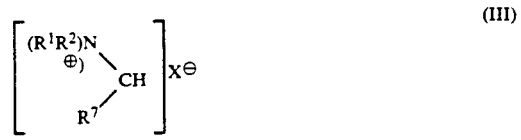

(III)

in the presence of alkoxides of the formula $$M^1OR^{10}$$  (IV)

where the radicals $R^1$ to $R^4$, $R^7$, $R^{10}$, $X^-$ and $M^1$ have the meaning mentioned in the description.

10 Claims, No Drawings

PROCESS FOR THE PREPARATION OF AMINOMETHYLENE COMPOUNDS

BACKGROUND OF THE INVENTION

1. Field of the Invention

The invention relates to the preparation of aminomethylene compounds by aminomethylenation of C—H acid compounds in a one-step reaction. Aminomethylene compounds, such as aminomethylenated dinitriles, cyanoacetic esters and malonic esters, are important $C_3$ or $C_4$ building blocks in the synthesis of heterocycles, such as, for example, pyrazole, pyridine and quinoline derivatives, which find application as pharmaceutical active compounds and plant protection agents (U.S. Pat. No. 4,620,865).

2. Description of the Related Art

It is known that C—H acid compounds can be aminomethylenated by reaction with dimethylformamide (DMF) and auxiliaries. If, for example, a ten-fold molar excess of acetic anhydride is used as the auxiliary, yields of 20 to 40% of the theoretical yield of aminomethylenated substances are obtained after heating for 5 to 7 hours under reflux (Arch. Pharm. 295 (1962), 516). With variation of the reaction conditions to improve the space-time yield, larger amounts of carbon monoxide are formed according to DD 151,624. If the acetic anhydride is replaced by $POCl_3$ and the reaction is carried out in excess DMF, about 47% of reaction product is obtained when using methyl cyanoacetate as the C-H acid compound (Z. obs. chim. 32 (1962), 4050, cited in DD 151,624). The conduct of the reaction and the working up are very complicated. If the variant mentioned is carried out using $POCl_3$ in benzene, only 7% of reaction product is isolated (Chem. Ber. 94 (1961), 2278). If ethyl chloroformate is used as the auxiliary, only 31% of the theoretical yield is obtained in the case of cyanoacetic ester on account of side reactions occurring. The use of phosgene gives 81% of the theoretical yield in the case of diethyl malonate using an excess of sodiomalonic ester as base. With ethyl cyanoacetate, 75% of the theoretical yield is obtained using triethylamine as base (Chem. Ber. 94 (1961), 2278). However, the use of sodiomalonic ester is expensive, on the other hand with triethylamine complicatedly large amounts of triethylamine hydrochloride have to be separated off.

According to DD 257,067, the reaction of cyanoacetate with the DMF-dimethylsulfate-adduct and sodium carbonate as the base leads to 53-61 % of the theoretical yield of the aminomethylenated product, however the non-uniform fusion point points to impurities.

Without base, the aminomethylenation can be carried out using thionyl chloride. In this case, the reaction mixture has to heated under reflux conditions in tetrachloromethane for 5 hours in order to obtain a yield of 79% of ethyl dimethylamino-cyanoacetate. However, the black crude product has to be recrystallized so that in the most favorable case (with a 25% excess of DMF and thionyl chloride) 68% of the theoretical yield of clean substance can be isolated (DD 151,624). Some tests showed that when using the less problematical solvent toluene 15% less reaction product is again obtained. An aminomethylenation of malonic ester is not possible by this method.

Additionally, in reactions with DMF and chlorinating agents, such as $PCl_5$, $POCl_3$, $SOCl_2$, $COCl_2$ and the like, the carcinogenic N,N-dimethylcarbamoyl chloride is formed as a secondary component, so that the handling and use of the product thus prepared is problematical; use is only possible after complicated purification steps.

Aminomethylenation using the combination Gold's salt/sodium methoxide leads after heating to reflux in ethanol overnight to a yield of 55 to 82% of the theoretical yield (Synth. Commun. 12 (1982), 939). Working up is complicated, and the reaction product still has to be additionally recrystallized. A large excess of DMF is required in order to prepare the Gold's salt. This and also the isolation of the salt is relatively cost-intensive, so that industrial production is too expensive.

Aminomethylenation with amidines or with the combination orthoester/sec.-amine is uneconomical because of the expensive reagents. Condensation with amide acetals and aminal esters is also unfavorable in terms of cost because of the troublesome manner of preparation of these orthoamides. DMF acetals are thus prepared by alkylation with alkyl sulphates (Chem. Ber. 96 (1963), 1350) and subsequent reaction with alkali metal alkoxides (Chem. Ber. 101 (1968), 41). The isolation from the alcoholic reaction mixture according to DD 94,359 is troublesome and time-consuming. A supposedly improved distillation process mentioned in this East German Patent is referred to in DD 151,624 already mentioned above as difficult to realize industrially. Additionally, it was not possible to achieve the high yield indicated in a reworking in a laboratory manner.

The aminal esters are accessible by reaction of the DMF-dialkyl sulphate adducts with dimethylamine and then with alkali metal alkoxides in hexane, cyclohexane or ether (Chem. Ber. 101 (1968), 41). The yields are 77 to 84% in condensations of C—H acid compounds with dimethylformamide-diethyl acetal, at most 89% with the methyl aminal ester; the acetal is accessible in 63% of the theoretical yield from the DMF-dimethyl sulphate adduct, while the methyl aminal ester is obtainable in 62% of the theoretical yield, starting from tetramethylformamidinium methylsulphate.

SUMMARY OF THE INVENTION

A process for the preparation of aminomethylene compounds of the formula

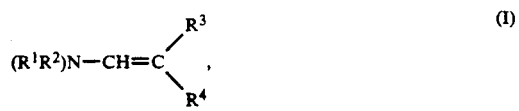

(I)

in which
R[1] and R[2] independently of one another represent straight-chain or branched $C_1$-$C_8$-alkyl, $C_2$-$C_8$-alkenyl, $C_2$-$C_8$-alkoxyalkyl, $C_3$-$C_8$-alkoxyalkenyl, $C_3$-$C_8$-cycloalkyl, $C_6$-$C_{12}$-aryl, $C_7$-$C_{10}$-aralkyl or a 5- to 8-membered saturated or unsaturated heterocyclic ring, heteroatoms 1 or 2 of which are from the group comprising N, O and S, it furthermore being possible for R[1] and R[2], together with the N atom which they substitute, to form a 5- to 8-membered saturated or unsaturated N-heterocyclic ring which can contain a further heteroatom from the group comprising N, O and S, and
R[3] and R[4] independently of one another denote $C_6$-$C_{12}$-aryl, $-NO_2$, $-CN$, $-NC$, $COR^5$, $CSR^5$, $CO-OR^5$, $CO-SR^5$ or $CO-N(R^5, R^6)$, in which R[5] and R[6] assume the scope of meaning given for $R^1$ and $R^2$, but are independent of $R^1$ and $R^2$ and can additionally denote hydrogen, has been found, which is characterized in that C—H acid compounds of the formula

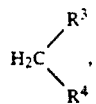 (II)

in which $R^3$ and $R^4$ have the meaning mentioned, are reacted with salts of the formula

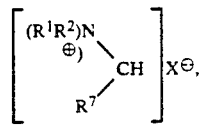 (III)

in which $R^1$ and $R^2$ have the meaning mentioned, $R^7$ represents —$OR^8$ or —$N(R^8, R^9)$, in which $R^8$ and $R^9$ independently of one another and independently of $R^1$ and $R^2$ have the scope of meaning mentioned for $R^1$ and $R^2$ and $X^\ominus$ denotes the $C_1$-$C_8$-alkylsulphate anion, the $C_6$-$C_{12}$-arylsulphonate anion, the tetrafluoroborate anion or the hexachloroantimonate anion, in the presence of alkoxides of the formula

$M^1OR^{10}$ (IV)

in which $R^{10}$ denotes straight-chain or branched $C_1$-$C_8$-alkyl, $C_2$-$C_8$-alkenyl, $C_2$-$C_8$-alkoxyalkyl, $C_3$-$C_8$-alkoxyalkenyl, $C_3$-$C_8$-cycloalkyl, $C_2$-$C_8$-alkylene-$OM^1$ or $C_7$-$C_{10}$-aralkyl and $M^1$ is an equivalent of an alkali metal cation or an alkaline earth metal cation, in a one-step reaction at a temperature of 10° to 70° C., preferably 20° to 60° C.

DETAILED DESCRIPTION OF THE INVENTION

Straight-chain or branched $C_1$-$C_8$-alkyl is, for example, methyl, ethyl, propyl, isopropyl, butyl, isobutyl, tert.-butyl, or the isomeric amyls, hexyls or octyls, preferably the $C_1$-$C_4$-alkyl radicals mentioned.

$C_2$-$C_8$-alkenyl is vinyl, propenyl, allyl, or the isomeric butenyls, amylenyls, hexenyls or octenyls, preferably the $C_3$-$C_4$-alkenyl radicals mentioned.

$C_2C_8$-alkoxyalkyl is, for example, methoxymethyl, ethoxymethyl, methoxyethyl and other radicals from the group comprising $C_3$-$C_8$ alkyl in which a C atom is replaced by an O atom.

$C_3$-$C_8$-alkoxyalkenyl is, for example, methoxyvinyl, ethoxyvinyl, methoxyallyl, 2-methoxy-propenyl and others from the group comprising $C_4$-$C_8$-alkenyl, in which a C atom is replaced by an O atom.

$C_3$-$C_8$-cycloalkyl is, for example, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl, preferably cyclopropyl, cyclopentyl and cyclohexyl and their methyl or dimethyl derivatives.

$C_6$-$C_{12}$-aryl is, for example, phenyl, naphthyl or biphenylyl, preferably phenyl.

$C_7$-$C_{10}$-aralkyl is, for example, benzyl, 1-phenylethyl, 2-phenyl-ethyl and other radicals of this type known to the person skilled in the art, preferably benzyl.

A 5- to 8-membered saturated or unsaturated heterocyclic ring, heteroatoms 1 or 2 of which are from the group comprising N, O and S, which may be mentioned is: pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine.

It is known to the person skilled in the art that unsaturated heterocyclic rings can have a more or less strongly pronounced aromatic character.

$R^1$ and $R^2$, together with the N atom which they substitute, may furthermore form a 5- to 8-membered saturated or unsaturated (optionally aromatic) N-heterocyclic ring which may contain a further heteroatom from the group comprising N, O and S. Systems of this type are, for example, pyrrole, pyrrolidine, pyrroline, pyrazole, pyrazolidine, imidazole, imidazolidine, thiazole, thiazolidine, piperazine, piperidine, morpholine, azepine and dihydroazocine.

The $C_1$-$C_8$ alkyl sulphate anion is, for example, the anion of methylsulphuric acid, ethylsulphuric acid, propylsulphuric acid, isopropylsulphuric acid, butylsulphuric acid, isobutylsulphuric acid, or one of the isomeric hexylsulphuric acids or octylsulphuric acids.

The $C_6$-$C_{12}$-arylsulphonate anion is, for example, the anion of benzenesulphonic acid, naphthalene-sulphonic acid or biphenyl-sulphonic acid, preferably benzenesulphonic acid.

$X^\ominus$ is preferably alkylsulphate, particularly preferably methylsulphate.

$M^1$ is an equivalent of an alkali metal or alkaline earth metal cation, for example the cation of lithium, sodium, potassium, rubidium, caesium, magnesium, calcium, strontium or barium; preferably the cation of an alkali metal, particularly preferably the cation of sodium or potassium.

In the case in which $R^{10}$ represents $C_2$-$C_8$-alkylene-$OM^1$, it is the alkoxide of a diol having 2 to 8 C atoms, such as glycol, 1,2-propanediol, 1,3-propanediol, 1,2-, 1,3- or 1,4-butanediol, hexanediol or octanediol.

Under the salts of the formula (III) used for the reaction according to the invention come alkoxymethyleneiminium salts of the formula

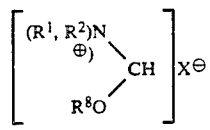 (IIIa)

and formamidinium salts of the formula

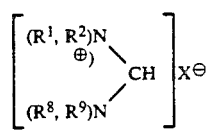 (IIIb)

having the abovementioned substituents.

The reaction according to the invention can be represented by way of example as follows:

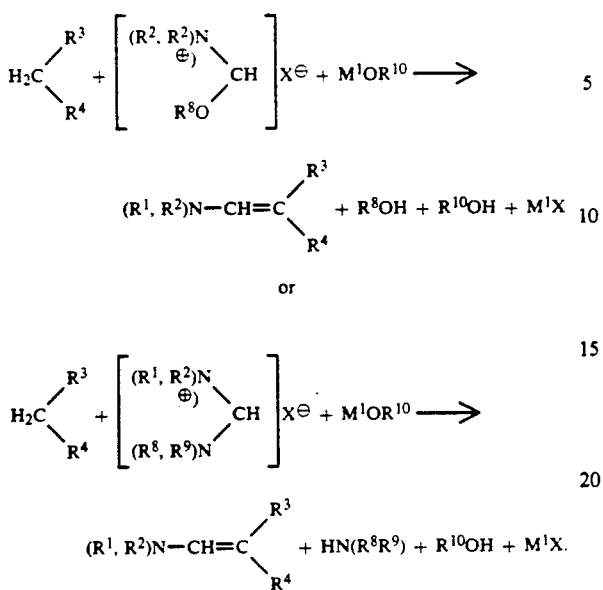

$R^8$ and $R^9$ have the scope of meaning of $R^1$ or $R^2$, but are independent of $R^1$ and $R^2$. If $R^8$ and $R^9$ are different from $R^1$ or $R^2$, those radicals $R^8$ and $R^9$ are chosen which enable the N atom carrying them to be split off as $HN(R^8, R^9)$. This can be determined by simple preliminary tests. In a preferred manner, however, $R^8$ and $R^9$ are equal to $R^1$ and $R^2$ so that a symmetrical formamidinium salt is present.

In a preferred manner, a C—H acid compound of the formula $$H_2C\begin{matrix}R^{13}\\R^{14}\end{matrix} \qquad (V)$$

is employed n which $R^{13}$ and $R^{14}$ independently of one another denote phenyl, $NO_2$, CN, $COR^{15}$, $COOR^{15}$ or CO—$N(R^{15}, R^{16})$, where $R^{15}$ and $R^{16}$ independently of one another represent hydrogen, straight-chain or branched $C_1$-$C_8$-alkyl, cyclopropyl, cyclopentyl, cyclohexyl, phenyl or benzyl and $R^{15}$ and $R^{16}$, together with the N atom which they substitute, can form a 5- to 8-membered saturated or unsaturated N-heterocyclic ring which can contain a further heteroatom from the group comprising N, O and S.

In a particularly preferred manner, a C—H acid compound of the formula $$H_2C\begin{matrix}R^{23}\\R^{24}\end{matrix} \qquad (VI)$$

is employed in which $R^{23}$ and $R^{24}$ independently of one another denote phenyl, $NO_2$, CN, $COR^{25}$, $COOR^{25}$ or CO—$N(R^{25}, R^{26})$, where $R^{25}$ and $R^{26}$ independently of one another denote hydrogen or straight-chain or branched $C_1$-$C_4$-alkyl and furthermore where $R^{25}$ and $R^{26}$, together with the N atom which they substitute, can denote morpholino, pyrrolidino or piperidino.

In a furthermore preferred manner, the C—H acid compounds are reacted with a salt of the formula

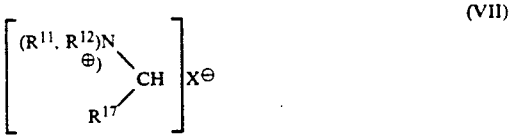

in which $R^{11}$ and $R^{12}$ independently of one another denote straight-chain or branched $C_1$-$C_8$-alkyl, cyclopropyl, cyclopentyl, cyclohexyl, phenyl or benzyl and $R^{11}$ and $R^{12}$ furthermore, together with the N atom which they substitute, can form a 5- to 8-membered saturated or unsaturated N-heterocyclic ring which can contain a further heteroatom from the group comprising N, O and S, represents —$OR^{11}$ or —$N(R^{11}, R^{12})$ and $X^\ominus$ denotes the $C_1$-$C_8$-alkylsulphate anion, the $C_6$-$C_{12}$-arylsulphonate anion, the tetrafluoroborate anion or the hexachloroantimonate anion.

Furthermore, the C—H acid compounds are reacted in a particularly preferred manner with a salt of the formula

in which $R^{21}$ and $R^{22}$ independently of one another denote straight-chain or branched $C_1$-$C_4$-alkyl and $R^{21}$ and $R^{22}$ furthermore, together with the N atom which they substitute, can denote morpholino, pyrrolidino or piperidino, $R^{27}$ represents —$OR^{21}$ or —$N(R^{21}, R^{22})$ and $X^{1\ominus}$ denotes the $C_1$-$C_8$-alkylsulphate anion.

In a furthermore preferred manner, the reaction is carried out in the presence of an alkoxide of the formula $$M^2OR^{20} \qquad (IX)$$

in which $R^{20}$ represents straight-chain or branched $C_1$-$C_5$-alkyl, $C_2$-$C_5$-alkoxyalkyl or $C_2$-$C_4$-alkylene-$OM^2$ and $M^2$ denotes $Na^\oplus$ or $K^\oplus$.

In a furthermore particularly preferred manner, the reaction is carried out in the presence of an alkoxide of the formula $$M^2OR^{30} \qquad (X)$$

in which $R^{30}$ represents straight-chain or branched $C_1$-$C_5$-alkyl and $M^2$ has the above meaning.

In a very particularly preferred manner, the substituents $R^1$, $R^2$, $R^8$, $R^9$ and $R^{10}$ denote the methyl radical. In a furthermore very particularly preferred manner, $X^{1\ominus}$ denotes the $C_1$-$C_4$-sulphate anion, preferably the methylsulphate anion.

The C—H acid compound, the salt and the alkoxide (III) are in general employed in a molar ratio of 1:1:1 to 1:2.5:2. In a preferred manner, the ratio 1:1.1:1.05 to 1:1.7:1.2 is chosen. With malonic esters, it may be necessary to employ an amount of salt in the upper part of the range mentioned; in the case of reactions with malonic esters, the aminomethylenated reaction product is obtained together with the unreacted salt as a two-phase system, as a result of which separation and recycling of the salt is simplified.

It is a characteristic of the process according to the invention that the mixture of the salt (alkoxymethyleneiminium salt or tetraalkylformamidinium salt) and the C—H acid compound is reacted with a solution or suspension of the alkoxide in a single process step. In this case, in spite of the risk of unpredictable side reactions, the advantage of a considerable increase in the yield is obtained.

If the salt and the C—H acid compound employed are not miscible, a solvent can be used and the solution resulting therefrom or an emulsion kept homogeneous by stirring can be employed. It is furthermore possible to meter in both components (salt and C—H acid compound) simultaneously to the initially introduced alkoxide or to meter salt, C—H acid compound and alkoxide simultaneously into the reaction vessel.

Solvents used are hydrocarbons, such as toluene, xylene, cyclohexane or petroleum ether, alcohols, carbonyl compounds or ethers. Such solvents can also be employed as a mixture. In the case of the use of a non-polar medium (for example toluene), the alkoxide is in general suspended therein; the other reaction components are metered into this suspension in the manner described above.

In such a case, the alkoxide is consumed during the ensuing reaction. The resulting salt precipitates and can be separated off from the reaction product dissolved in the reaction medium in a simple manner. If the reaction is carried out in an alcoholic medium, the alkoxide is in general in dissolved form. However, the resulting salts are also at least partially soluble in lower alcohols. A nearly complete separation of the resulting salts and the resulting reaction product is achieved by means of a mixture of a non-polar solvent and the alcoholic alkoxide solution.

If the C—H acid compound used contains an ester group, it is advantageous to take an alkoxide whose underlying alcohol corresponds to the ester alcohol; undesired transesterifications are avoided in this way.

If the C—H acid compound contains, for example, a nitrile substituent, this is not attacked under the mild reaction conditions (for example 0.5 to 2 h and 20° to 70° C.). Even higher temperatures are briefly possible, for example for incipient distillation.

If the methylsulphate salts of the alkoxymethyleneiminium ions or formamidinium ions are employed, the alkoxide employed is surprisingly not methylated by the anion, even at a relatively high temperature, as a result of which yield reductions are avoided.

The yields in the process according to the invention are very high with about 90 to 98% of the theoretical yield; as a result of this the reaction product is very pure and can in general be used directly for further reactions. With the formamidinium salts, around 1 to 20% higher yields can be attained than with the alkoxymethyleneiminium salts, depending on the C—H acid compound. Since the former can be prepared from the latter in nearly quantitative yield by reaction with a secondary amine, the more economical process can be chosen, depending on the aminomethylenation yield.

EXAMPLE 1

An emulsion of 66.0 g of dimethyl malonate and 116.6 g of tetramethylformamidinium methylsulphate were initially introduced into 300 ml of dry toluene. 104 ml of a 30% strength sodium methoxide solution were added dropwise with the exclusion of moisture in the course of 10 min. and the mixture was stirred at room temperature for 1 h. The sodium methylsulphate (67.4 g) formed was then filtered off with suction and washed twice with 30 ml portions of toluene, and the filtrate was concentrated on a rotary evaporator. 104.5 g of 84.1% pure dimethylaminomethylenemalonic ester were obtained, which corresponds to 94.0% of the theoretical yield. The product could be used crude for a further reaction without disadvantages compared to distilled material.

EXAMPLE 2

68.5 g of an approximately 30% strength sodium isobutoxide solution, which was additionally diluted with 200 ml of isobutanol, were added dropwise to a solution of 55.3 g of tetramethylformamidinium methylsulphate and 43.2 g of diisobutyl malonate. After 90 min. at 70° C., the salt was filtered off with suction and washed twice with 20 ml portions of isobutanol, and the filtrate was concentrated on a rotary evaporator. The lower phase, which principally consisted of the formamidinium salt, was removed with the aid of a pipette. The residue (53.8 g) consisted to 98.8% of dimethylaminomethylenemalonic ester, which corresponds to 98.1% of the theoretical yield.

EXAMPLE 3

Aminomethylenation was carried out with 54 g of dimethylformamide-dimethyl sulphate adduct analogously to Example 2. The adduct was added dropwise at 0° C. and then warmed at 50° C. for 3 h. 53.5 g of 91.6% pure product were obtained, corresponding to a yield of 90.4% of the theoretical yield.

EXAMPLE 4

A mixture of 25.4 g of tetramethylformamidinium methylsulphate and 11.3 g of ethyl cyanoacetate was added dropwise to a suspension of 7.5 g of sodium ethoxide in 100 ml of dry toluene. After 1 h at 40° C., sodium methylsulphate was filtered off with suction at 50° C. and washed twice with 15 ml portions of toluene, and the filtrate was concentrated on a rotary evaporator. 17.2 g of 94.3% pure pale yellow product were obtained, corresponding to 98.5% of the theoretical yield. After recrystallization from aqueous isopropanol, white crystals of melting point 80° C. could be obtained.

EXAMPLE 5

Corresponding to Example 4, 9.9 g of methyl cyanoacetate were reacted with 26.5 g of formamidinium salt and 5.4 g of sodium methoxide in 180 ml of toluene. 15.0 g of 92.7% pure product were obtained, corresponding to 93.2% of the theoretical yield. The sodium methylsulphate filtered off with suction contained a further 2% of the theoretical yield.

EXAMPLE 6 (For Comparison)

0.5 mol of DMF-dimethyl sulphate adduct was added dropwise at 0° C. to 0.5 mol of a 3-molar sodium methoxide solution in ethanol. After stirring at 20° C. for 2 h, the bulk was distilled off and the residue was then distilled further while adding ethanol dropwise to the salt magma. After 300 ml of ethanol had been recycled, the distillate was fractionated with the aid of a packed column. 47 g of DMF acetal were obtained, corresponding to a 63.9% yield.

147 g of DMF diethyl acetal together with 149 g of diethyl malonate were heated at 140° to 150° C. for 4 h in a stirring flask fitted with a column. 82 g of ethanol distilled over in the course of this. The reaction mixture was then fractionated in a high vacuum and 164 g, corresponding to 82% of the theoretical yield of dimethylaminomethylenemalonic ester, were obtained.

What is claimed is:

1. A process for the preparation of an aminomethylene compound of the formula

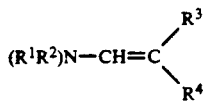

in which
R$^1$ and R$^2$ independently of one another represent straight-chain or branched C$_1$-C$_8$-alkyl, C$_2$-C$_8$-alkenyl, C$_2$-C$_8$-alkoxyalkyl, C$_3$-C$_8$-alkoxyalkenyl, C$_3$-C$_8$-cycloalkyl, C$_6$-C$_{12}$-aryl or C$_7$-C$_{10}$-aralkyl it furthermore being possible for R$^1$ and R$^2$, together with the N atom which they substitute, to denote morpholino, pyrrolidino or piperidino, and
R$^3$ and R$^4$ independently of one another denote C$_5$-C$_{12}$-aryl, —NO$_2$, —CN, —NC, COR$^5$, CSR$^5$, CO—OR$^5$, CO—SR$^5$ or CO—N(R$^5$, R$^6$), in which R$^5$ and R$^5$ assume the scope of meaning give for R$^1$ and R$^2$, but are independent of R$^1$ and R$^2$ and can additionally denote hydrogen, and at least one of R$^3$ and R$^4$ is CN or COOR$^5$,
which comprises reacting a C—H acid compound of the formula

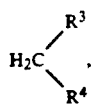

with a salt of the formula,

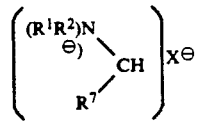

(III)

in which
R$^7$ represents —OR$^8$ or —N(R$^8$, R$^8$), in which R$^8$ and R$^8$ independently of one another and independently of R$^1$ and R$^2$ have the scope of meaning mentioned for R$^1$ and R$^2$ and
X$^\ominus$ denotes the C$_1$-C$_8$-alkylsulphate anion, the C$_6$-C$_{12}$-arylsulphonate anion, the tetrafluoroborate anion or the hexachloroantimonate anion,
in the presence of an alkoxide of the formula

M$^1$OR$^{10}$ in which
R$^{10}$ denotes straight-chain or branched C$_1$-C$_8$-alkyl, C$_2$-C$_8$-alkenyl, C$_2$-C$_8$-alkoxyalkyl, C$_3$-C$_8$-alkox-
yalkenyl, C$_3$-C$_8$-cycloalkyl, C$_2$-C$_8$-alkylene-OM$^1$ or C$_7$-C$_{10}$-aralkyl and
M$^1$ is an equivalent of an alkali metal cation or an alkaline earth metal cation,
in a one-step reaction at a temperature of 10° to 70° C., the C—H acid compound, the salt and the alkoxide being employed in a molar ratio of 1:1:1 to 1:2.5:2.

2. The process of claim 1, which is carried out at 20° to 60° C.

3. The process of claim 1,
in which
R$^3$ and R$^4$ independently of one another denote phenyl, NO$_2$, CN, COR$^{15}$, COOR$^{15}$ or CO—N(R$^{15}$, R$^{16}$), where R$^{15}$ and R$^{16}$ independently of one another represent hydrogen, straight-chain or branched C$_1$-C$_8$-alkyl, cyclopropyl, cyclopentyl, cyclohexyl, phenyl or benzyl or R$^{15}$ and R$^{16}$, together with the N atom which they substitute, denote morpholino, pyrrolidino or piperidino, and at least one of them is CN or COOR$^5$.

4. The process of claim 3, wherein a C—H acid compound of the formula

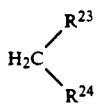

is employed in which
R$^{23}$ and R$^{24}$ independently of one another denote phenyl, NO$_2$, CN, COR$^{25}$, COOR$^{25}$ or CO—N(R$^{25}$, R$^{26}$), where R$^{25}$ and R$^{26}$ independently of one another denote hydrogen or straight-chain or branched C$_1$-C$_4$-alkyl or R$^{25}$ and R$^{26}$, together with the N atom which they substitute, can denote morpholino, pyrrolidino or piperidino and at least one of R$^3$ and R$^4$ is CN or COOR$^5$.

5. The process of claim 1, wherein the C—H acid compound is reacted with a salt of the formula

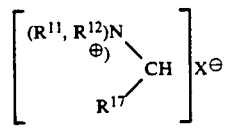

in which
R$^{11}$ and R$^{12}$ independently of one another denote straight-chain or branched C$_1$-C$_8$-alkyl, cyclopropyl, cyclopentyl, cyclohexyl, phenyl or benzyl and R$^{11}$ and R$^{12}$ furthermore, together with the N atom which they substitute, can denote morpholino, pyrrolidino or piperidino,
R$^{17}$ represents —OR$^{11}$ or —N(R$^{11}$, R$^{12}$) and denotes the C$_1$14 C$_8$-alkylsulphate anion, the C$_6$-C$_{12}$-arylsulphonate anion, the tetrafluoroborate anion or the hexachloroantimonate anion.

6. The process of claim 5, wherein the C—H acid compound is reacted with a salt of the formula

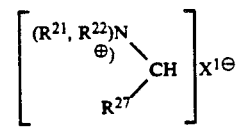

in which

R$^{21}$ and R$^{22}$ independently of one another denote straight-chain or branched C$_1$-C$_4$-alkyl and R$^{21}$ and R$^{22}$ furthermore, together with the N atom which they substitute, can denote morpholino, pyrrolidino or piperidino, R$^{27}$ represents —OR$^{21}$ or —N(R$^{21}$, R$^{22}$) and X$^{1\ominus}$ denotes the C$_1$-C$_8$-alkylsulphate anion.

7. The process of claim 1, which is carried out in the presence of an alkoxide of the formula $$M^2OR^{20}$$

in which

R$^{20}$ represents straight-chain or branched C$_1$-C$_5$-alkyl, C$_2$-C$_5$-alkoxyalkyl or C$_2$-C$_4$-alkylene-OM$^2$ and M$^2$ denotes Na$^\oplus$ or K$^\oplus$.

8. The process of claim 7, which is carried out in the presence of an alkoxide of the formula $$M^2OR^{30}$$

in which

R$^{30}$ represents straight-chain or branched C$_1$-C$_5$-alkyl and

M$^2$ denotes Na$^\oplus$ or K$^{61}$.

9. The process of claim 1, wherein the C—H acid compound, the salt and the alkoxide are employed in a molar ratio of 1:1.1:1.05 to 1:1.7:1.2.

10. The process of claim 1, wherein a formamidinium salt is employed as the salt.

* * * * *

UNITED STATES PATENT AND TRADEMARK OFFICE
CERTIFICATE OF CORRECTION

PATENT NO. : 5,095,133
DATED : March 10, 1992
INVENTOR(S) : Blank et al.

It is certified that error appears in the above-indentified patent and that said Letters Patent is hereby corrected as shown below:

| | |
|---|---|
| Title Page | OTHER PUBLICATIONS: Line 5 delete " Orghoamides " and substitute -- Orthoamides-- |
| Col. 6, line 21 | Before " represents " insert -- $R^{17}$ -- |
| Col. 9, lines 56-57 | Delete " $-N(R^8, R^8)$, in which $R^8$ and $R^8$ " and substitute -- $-N(R^8, R^9)$, in which $R^8$ and $R^9$ -- |
| Col. 10, line 57 | Delete " 14 " and substitute -- - -- |
| Col. 12, claim 8 line 7 | Delete " $K^{61}$ " and substitute -- $K^{\circledcirc}$ -- |

Signed and Sealed this

Twenty-fifth Day of January, 1994

Attest:

BRUCE LEHMAN

*Attesting Officer*  *Commissioner of Patents and Trademarks*